(12) United States Patent
Yada et al.

(10) Patent No.: US 7,135,594 B2
(45) Date of Patent: Nov. 14, 2006

(54) METHOD FOR PREVENTING CLOGGING IN APPARATUS FOR HANDLING (METH)ACRYLIC ACID OR ESTERS THEREOF

(75) Inventors: Shuhei Yada, Yokkaichi (JP); Yasushi Ogawa, Yokkaichi (JP); Kenji Takasaki, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/000,505

(22) Filed: Dec. 1, 2004

(65) Prior Publication Data

US 2005/0215813 A1    Sep. 29, 2005

Related U.S. Application Data

(63) Continuation of application No. PCT/JP04/11445, filed on Aug. 9, 2004.

(30) Foreign Application Priority Data

Mar. 23, 2004  (JP) ............................. 2004-083954

(51) Int. Cl.
*C07C 57/02* (2006.01)
*C07C 69/52* (2006.01)

(52) U.S. Cl. ...................................... 560/205; 562/598

(58) Field of Classification Search .................. None
See application file for complete search history.

(56) References Cited

FOREIGN PATENT DOCUMENTS

JP          2003-231661     *   8/2003

* cited by examiner

*Primary Examiner*—Paul A. Zucker
(74) *Attorney, Agent, or Firm*—Nixon & Vanderhye P.C.

(57) ABSTRACT

There is provided a method for preventing clogging in an apparatus for handling (meth)acrylic acid or esters thereof which is capable of inhibiting occurrence of clogging in nozzles or conduits connected to a gas-phase portion of the apparatus and ensuring a stable continuous operation of the apparatus for a long period of time. The method for preventing clogging in an apparatus for handling (meth)acrylic acid or esters thereof, comprises blowing a gas having a polymerization inhibiting action into a nozzle or conduit connected to a gas-phase portion of the apparatus, wherein said gas having a polymerization inhibiting action, which is blown into the nozzle or conduit, has a temperature not less than a temperature of the gas-phase portion.

5 Claims, 1 Drawing Sheet

METHOD FOR PREVENTING CLOGGING IN APPARATUS FOR HANDLING (METH)ACRYLIC ACID OR ESTERS THEREOF

This application is a continuation of international application PCT/JP2004/11445, filed Aug. 9, 2004, which designated the U.S. and claims benefit of JP 2004-083954, dated Mar. 23, 2004, the entire contents of each of which is hereby incorporated by reference.

TECHNICAL FIELD

The present invention relates to a method for preventing clogging in an apparatus for handing (meth)acrylic acid or esters thereof, and more particularly to a method for preventing clogging in an apparatus for handing (meth)acrylic acid or esters thereof by blowing a gas having a polymerization inhibiting action into a nozzle or conduit connected to a gas-phase portion of the apparatus. Meanwhile, in the present specification, the "(meth)acrylic acid" generally includes acrylic acid and methacrylic acid, and the "(meth) acrylic esters" generally include acrylic esters and methacrylic esters.

BACKGROUND ARTS

The (meth) acrylic acid and esters thereof are easily-polymerizable compounds. In the processes for production and use of these compounds, undesired polymerization of the compounds tends to be frequently caused in handling apparatuses therefor such as distillation columns, evaporators, heat exchangers, tanks or the like, resulting in stoppage of the operation of these handling apparatuses.

In order to ensure a stable continuous operation of the apparatuses for handing (meth)acrylic acid and esters thereof, it has been inevitably required to measure process conditions such as pressure, temperature, liquid level or the like. For the purpose of measuring the process conditions, measuring devices are fitted to the above apparatuses through nozzles or the like. In these nozzles or the like, especially in the nozzles connected to gas-phase portions of the apparatuses, there have been frequently observed production of polymers of (meth)acrylic acid and esters thereof.

In order to prevent production of the polymers of (meth) acrylic acid and esters thereof, a polymerization inhibitor such as hydroquinone and copper-containing compounds is introduced into the apparatuses. However, these polymerization inhibitors introduced are present only in a liquid phase within the apparatuses, and are not contained in a gas phase therein. In order to prevent production of the polymers in the gas phase portion of the apparatuses, there is known the method of blowing a gas having a polymerization inhibiting action such as an oxygen-containing gas, for example, a mixed gas obtained by mixing an inert gas such as nitrogen, carbon dioxide gas and argon with air, or air into the handling apparatuses (Japanese Patent Application Laid-open (KOKAI) No. 2003-231661).

However, in practice, the above conventional method fails to completely prevent troubles due to production of the polymers of (meth)acrylic acid or esters thereof. According to the present inventors' knowledge, the reason therefor is that since the gas having a polymerization inhibiting action which is introduced into the apparatuses has a low temperature, the (meth)acrylic acid or esters thereof tend to be condensed in a gas phase portion thereof, so that polymers of these compounds tend to be produced in a condensed solution thereof containing no polymerization inhibitor, which is formed in the gas-phase portion.

DISCLOSURE OF THE INVENTION

Problem to be Solved by the Invention

The present invention has been achieved for solving these conventional problems. An object of the present invention is to provide a method for preventing clogging in an apparatus for handling (meth)acrylic acid and esters thereof which is capable of inhibiting occurrence of clogging in nozzles or conduits connected to a gas-phase portion of the apparatus and ensuring a stable continuous operation of the apparatus for a long period of time.

Means for Solving the Problem

The present invention has been attained on the basis of the above finding. To accomplish the aim, in a first aspect of the present invention, there is provided a method for preventing clogging in an apparatus for handling (meth)acrylic acid or esters thereof, comprising:

blowing a gas having a polymerization inhibiting action into a nozzle or conduit connected to a gas-phase portion of the apparatus, wherein said gas having a polymerization inhibiting action, which is blown into the nozzle or conduit, has a temperature not less than a temperature of the gas-phase portion.

Effect of the Invention

According to the method of the present invention, nozzles or conduits connected to the apparatus for handling (meth) acrylic acid or esters thereof can be effectively prevented from suffering from clogging due to polymers of these compounds, etc., so that the apparatus for handling (meth) acrylic acid or esters thereof can be stably operated at a high efficiency for a long period of time.

PREFERRED EMBODIMENT FOR CARRYING OUT THE INVENTION

Figure 1:
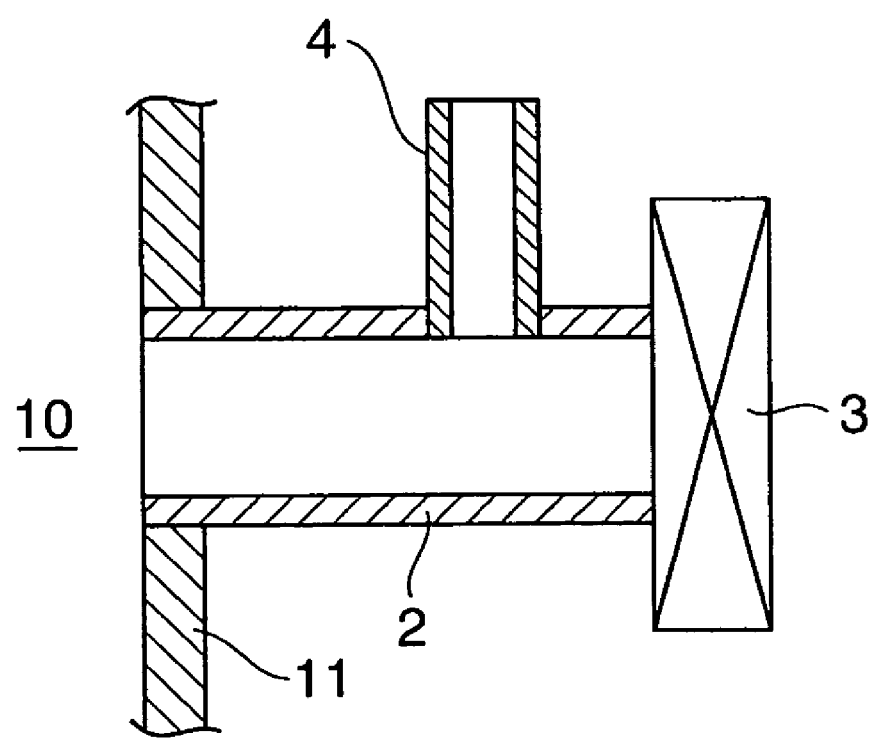
FIG. 1 is an explanatory view showing, partially in cross section, a fitting condition of an inlet for blowing a clogging-preventive gas into equipments attached to a distillation column used in the present invention.

The present invention is described in detail below. First, the general process for producing acrylic acid is explained. Acrylic acid can be produced by any of the following processes (1) to (3).

(1) A process comprising an oxidation step of subjecting propane, propylene and/or acrolein to gas-phase catalytic oxidation; a collection step of contacting the resultant acrylic acid-containing gas with water to collect acrylic acid in the form of an aqueous solution thereof; an extraction step of extracting acrylic acid from the thus obtained aqueous acrylic acid solution using an extraction solvent; a removing step, after distilling the obtained acrylic acid-containing solution to separate the solution into acrylic acid and the solvent, of removing low-boiling components from the obtained acrylic acid; and a purification step of further distilling the obtained acrylic acid.

(2) A process comprising an oxidation step of subjecting propane, propylene and/or acrolein to gas-phase catalytic oxidation; a collection step of contacting the resultant acrylic acid-containing gas with water to collect acrylic acid in the form of an aqueous solution thereof; an azeotropic separation step of distilling the thus obtained aqueous acrylic acid solution in the presence of an azeotropic agent in an azeotropic separation column and removing an acrylic acid-containing solution from a bottom of the column; a separation step of distilling the thus obtained acrylic acid-containing solution to remove acetic acid therefrom; and a purification step of further distilling the obtained acrylic acid.

(3) A process comprising an oxidation step of subjecting propane, propylene and/or acrolein to gas-phase catalytic oxidation; a collection/separation step of contacting the resultant acrylic acid-containing gas with an organic solvent to collect acrylic acid in the form of an organic solvent solution of acrylic acid, and simultaneously to remove water and acetic acid therefrom; and a distillation step of distilling the thus obtained organic solvent solution of acrylic acid.

Although the details of the process for production of (meth)acrylic esters are omitted herein, the (meth)acrylic esters may be produced, for example, by the process comprising an esterification reaction step of reacting (meth) acrylic acid with alcohol in the presence of a catalyst such as organic acids and cationic ion exchange resins, and a step of subjecting the thus obtained crude (meth)acrylic ester solution to extraction, evaporation and distillation in order to obtain the esters as a fraction distilled from a top of the column.

Examples of the thus obtained (meth)acrylic esters may include methyl (meth)acrylate, ethyl (meth)acrylate, n-propyl (meth)acrylate, isopropyl (meth)acrylate, n-butyl (meth) acrylate, isobutyl (meth)acrylate, 2-ethylhexyl (meth)acrylate, isononyl (meth)acrylate, n-nonyl (meth)acrylate, hydroxyethyl (meth)acrylate, ethoxyethyl (meth)acrylate and dimethoxyaminoethyl (meth)acrylate.

The apparatus for handling (meth)acrylic acid or esters thereof (hereinafter referred to merely as "handling apparatus") which is usable in the process of the present invention, may involve all of apparatuses used for producing the (meth)acrylic acid or esters thereof and preserving the thus produced (meth)acrylic acid or esters thereof. Examples of the handling apparatus may include reactors, distillation columns, collection columns, evaporators, heat exchangers, tanks, extraction vessels, decomposition reactors, etc. Of these apparatuses, typical ones are distillation columns and decomposition reactors, especially distillation columns.

Examples of the distillation columns may include a perforated plate columns, bubble-cap columns, packed columns and combinations of these columns (for example, combination of the perforated plate column and the packed column). These distillation columns may be used irrespective of provision of overflow weirs or down corners.

Examples of the trays used in the distillation columns may include trays having a downcomer such as a bubble-cap tray, a perforate plate tray, a bubble tray, a super-flux tray and a max-flux tray, and trays having no downcomer such as a dual tray.

Examples of the packing material used in the distillation column may include conventional packing materials having various shapes such as a solid cylindrical shape, a hollow cylindrical shape, a saddle shape, a spherical shape, a cubic shape and a pyramidal shape as well as recently commercially available regular or irregular high-performance packing materials having specific shapes.

Examples of the regular packing materials may include gauze-type regular packing materials such as "SULZER PACKING" produced by Sulzer Brothers Limited, "SUMITOMO SULZER PACKING" produced by Sumitomo Heavy Industries Ltd. and "TECHNOPACK" produced by Mitsui Bussan Co., Ltd.; sheet-type regular packing materials such as "MELAPACK" produced by Sumitomo Heavy Industries Ltd., "TECHNOPACK" produced by Mitsui Bussan Co., Ltd., and "M.C. PACK" produced by Mitsubishi Kagaku Engineering Co., Ltd.; and grid-type regular packing materials such as "FLEXI-GRID" produced by Cork Inc.

Examples of the regular packing materials may further include "JEMPACK" produced by Grich Inc., "MONTZ-PACK" produced by Montz Inc., "GOODROLL PACKING" produced by Tokyo Special Wire Netting Co. Ltd., "HONEYCOMB PACK" produced NGK Insulators, Ltd., "IMPULSE PACKING" produced Nagaoka Corporation.

Examples of the irregular packing materials may include Rashig ring, "POLE-RING" produced by BASF AG, "CASCADE MINI-RING" produced by Mass-Transfer Inc., "IMTP" produced by Norton Inc., "INTERLOCKS SADDLE" produced by Norton Inc., "TERALET" produced by Nittetsu Kakoki Co., Ltd., "FLEXI-RING" produced by Nikki Co., Ltd., or the like.

These packing materials may be used in the combination of any two or more thereof, and may also be used in combination with conventionally used trays.

The operation procedures of the above distillation column may vary depending upon compositions of raw materials to be distilled, recovery rate, purity of acrylic acid distilled, etc. However, since the acrylic acid is an easily-polymerizable compound, the distillation temperature and pressure are preferably set as low as possible. More specifically, the temperature at a bottom of the distillation column is usually in the range of 60 to 100° C., and the pressure at a top of the distillation column is usually in the range of 1 to 27 kPa.

Meanwhile, upon the distillation, in order to prevent production of polymers of the (meth)acrylic acid or esters thereof, any known polymerization inhibitors may be added thereto. Examples of the polymerization inhibitors may include N-oxyl compounds such as tert-butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidino-oxyl, 4-hydroxy-2,2,6,6-tetramethylpiperidino-oxyl and 4,4',4"-tris 1-(2,2,6,6-tetramethylpiperidino-oxyl)phosphite; phenol compounds such as hydroquinone, methoquinone, pyrogallol, catechol and resorcin; phenothiazine compounds such as phenothiazine, bis-(α-methylbenzyl) phenothiazine, 3,7-dioctyl phenothiazine and bis-(α-dimethylbenzyl)phenothiazine; and copper compounds such as cupric chloride, copper acetate, copper carbonate, copper acrylate, copper dimethyldithiocarbamate, copper diethyldithiocarbamate and copper dibutyldithiocarbamate. These polymerization inhibitors may be used in the combination of any two or more thereof.

The nozzles or conduits connected to a gas-phase portion of the handling apparatus may be fitted therein with measuring devices for monitoring process conditions of the (meth)acrylic acid or esters thereof such as, for example, pressure, temperature, liquid level, etc. Examples of the measuring devices may include analyzers such as a pressure gauge, a level gauge, a thermometer, an oxygen analyzer and a pH meter.

Specific examples of the pressure gauge may include a diaphragm-type pressure gauge, a bellow-type pressure gauge and a Bourdon's tube-type pressure gauge. Specific examples of the thermometer may include a pyrometer, a resistance thermometer and a bimetal-type thermometer. Specific examples of the level gauge may include a pressure-type level gauge, a differential pressure-type level gauge and a gauge glass-type level gauge.

Meanwhile, the materials of a body of the handling apparatus as well as those of nozzles, reboilers, condensers, vent gas condensers, reflux tanks, conduits and pumps as attached equipments are not particularly restricted as long as these materials can exhibit a suitable anti-corrosion property against compounds to be handled under the temperature conditions thereof. Examples of the materials may include carbon steels, stainless steels such as SUS304, SUS304L, SUS316, SUS316L, SUS317, SUS317L and SUS327, and hastelloys.

The polymers that cause clogging in nozzles or conduits of the handling apparatus, are polymers of (meth)acrylic acid or esters thereof, which are derived from Michael adducts of these compounds, radical polymers of (meth) acrylic acid or esters thereof, etc.

Examples of the Michael adducts may include (i) Michael adducts of acrylic acid, (ii) Michael adducts of acrylic esters, and (iii) Michael adducts of alcohols. Specific examples of the Michael adducts (i) of acrylic acid may include acrylic acid dimers (hereinafter referred to merely as "dimers"), acrylic acid trimers (hereinafter referred to merely as "trimers"), acrylic acid tetramers (hereinafter referred to merely as "tetramers") and β-hydroxypropionic acid.

The Michael adducts (ii) of acrylic esters are compounds obtained by adding acrylic acid to the above acrylic esters such as alkyl esters having 2 to 8 carbon atoms or cycloalkyl esters of acrylic acid. Specific examples of the Michael adducts (ii) of acrylic esters may include β-acryloxypropionic acid esters such as methyl β-acryloxypropionate, ethyl β-acryloxypropionate, butyl β-acryloxypropionate and 2-ethylhexyl β-acryloxypropionate. The Michael adducts (iii) of alcohols are compounds obtained by adding alcohol or water to the acrylic esters. Specific examples of the Michael adducts (iii) of alcohols may include β-alkoxypropionic acid esters, esters of the dimers, trimers or tetramers, β-hydroxypropionic acid and β-hydroxypropionic acid esters.

The radical polymers of the (meth)acrylic acid or esters thereof are poly(meth)acrylic acid or esters thereof which are produced by cleaving C=C bonds of the (meth)acrylic acid or esters thereof, and bonding the thus cleaved compounds to each other. In the process for production of (meth)acrylic esters, since the (meth)acrylic acid is used as a raw material, the obtained radical polymers may be in the form of a copolymer of (meth)acrylic acid and the (meth) acrylic ester. Further, the radical polymers may also be in the form of Michael adduct polymers obtained by adding (meth) acrylic acid or its esters thereto.

The method for preventing clogging according to the present invention is characterized by blowing a gas having a polymerization inhibiting action to nozzles or conduits connected to a gas-phase portion of the handling apparatus at a temperature not less than the temperature of the gas-phase portion.

An example of the method for preventing clogging according to the present invention is explained by referring to FIG. 1. FIG. 1 is an explanatory view showing, partially in cross section, a fitting condition of an inlet for blowing a clogging-preventive gas into equipments attached to a distillation column used in the present invention.

A measuring device (3) is fitted onto a column wall (11) defining a gas-phase portion of a distillation column (10) through a nozzle (2). The nozzle (2) is provided with a gas blowing inlet (4) through which a gas having a polymerization inhibiting action is blown into the nozzle (2) at a temperature not less than the temperature of the gas-phase portion.

As the gas having a polymerization inhibiting action, there may be used an oxygen gas and/or a nitrogen oxide-containing gas. Specific examples of the gas having a polymerization inhibiting action may include a mixed gas of an inert gas with nitrogen oxide and/or air, air or the like. Examples of the inert gas may include nitrogen, argon, carbon dioxide and steam.

When the inert gas is used in combination with oxygen and/or nitrogen oxide, the volume ratio of the inert gas to oxygen and/or nitrogen oxide is usually 2:98 to 96:4.

The temperature of the gas having a polymerization inhibiting action is not less than the temperature of the gas-phase portion, preferably higher by 0 to 30° C. than the temperature of the gas-phase portion of the handling apparatus. When the temperature of the gas having a polymerization inhibiting action, which is blown into the gas-phase portion, is less than the temperature of the gas-phase portion, the (meth)acrylic acid or esters thereof tend to be condensed.

The method of heating the gas having a polymerization inhibiting action is not particularly restricted as long as the gas temperature as required can be ensured. For example, there may be used either a heating method using a heat exchanger, or a method of mixing the gas with a heated gas produced during or out of the process. Examples of the heat exchanger may include a vertical fixed tube plate-type heat exchanger, a horizontal fixed tube plate-type heat exchanger, a U-shaped tube-type heat exchanger, a double tube-type heat exchanger, a spiral-type heat exchanger, a rectangular block-type heat exchanger and a plate-type heat exchanger.

The blowing velocity of the gas having a polymerization inhibiting action is not particularly restricted as long as the gas temperature as required can be ensured. In addition, a diameter and fitting angle of the blowing nozzle, etc., are not particularly restricted as long as the gas temperature as required can be ensured.

EXAMPLES

The present invention is described in more detail by Examples, but the Examples are only illustrative and not intended to limit the scope of the present invention.

Example 1

An acrylic acid solution containing 2.9% by weight of acetic acid and 6% by weight of toluene was introduced into a distillation column having a column body diameter of 1,400 mm at a feed rate of 7.5 tons/h. The distillation column was operated at a top pressure of 6 kPa, a top temperature of 50° C. and a bottom temperature of 92° C., thereby obtaining acrylic acid containing no toluene and acetic acid from a bottom of the column. Pressure gauges were respectively fitted to ¾ inch nozzles provided in gas-phase portions of top and bottom of the column. While continuously blowing air heated to 53° C. (oxygen concentration: 21 mol %) and air heated to 98° C. (oxygen concentration: 21 mol %) into the nozzle provided at the top of the column and the nozzle provided at the bottom of the column, respectively, through blowing inlets at a flow rate of 0.02 m/s, the operation of the distillation column was continued. As a result, it was confirmed that the operation of the distillation column was stably performed for 6 months.

Comparative Example 1

The same procedure as defined in Example 1 was conducted except that the temperature of air blown into the nozzles through the blowing inlets was 24° C. (temperature of outside air). After 2 weeks from initiation of operation of the distillation column, the pressure value indicated on the pressure gauge was gradually raised. Therefore, after 4 weeks from initiation of operation of the distillation column, the operation of the distillation column was stopped to inspect an inside thereof. As a result, it was confirmed that the nozzles were clogged with polymers of acrylic acid.

Example 2

Using the same distillation column as used in Example 1, an acrylic acid ethyl ester solution containing 0.3% by weight of ethanol and 1.8% by weight of water was introduced thereinto at a feed rate of 6 tons/h. The distillation column was operated at a top pressure of 63 kPa, a top temperature of 76° C. and a bottom temperature of 90° C., thereby obtaining an acrylic acid ethyl ester containing no ethanol and water from a bottom of the column. Pressure gauges were respectively fitted to ¾ inch nozzles provided in gas-phase portions of top and bottom of the distillation column. While continuously blowing air heated to 78° C. (oxygen concentration: 6 mol %; nitrogen concentration: 94 mol %) and air heated to 95° C. (oxygen concentration: 6 mol %; nitrogen concentration: 94 mol %) into the nozzle provided at the top of the column and the nozzle provided at the bottom of the column, respectively, through blowing inlets at a flow rate of 0.01 m/s, the operation of the distillation column was continued. As a result, it was confirmed that the operation of the distillation column was stably performed for 3 months.

Comparative Example 2

The same procedure as defined in Example 2 was conducted except that the temperature of air blown into the nozzles through the blowing inlets was 24° C. (temperature of outside air). After 3 weeks from initiation of operation of the distillation column, the pressure values indicated on the pressure gauges were gradually raised. Therefore, after 5 weeks from initiation of operation of the distillation column, the operation of the distillation column was stopped to inspect an inside thereof. As a result, it was confirmed that the nozzles were clogged with polymers of an acrylic acid ethyl ester.

The invention claimed is:

1. A method for preventing clogging in an apparatus for handling (meth)acrylic acid or esters thereof, comprising:
    blowing a gas having a polymerization inhibiting action into a nozzle or conduit connected to a gas-phase portion of the apparatus, wherein said gas has a polymerization inhibiting action, is blown into the nozzle or conduit, has a temperature not less than a temperature of the gas-phase portion.

2. A method according to claim 1, wherein said gas having a polymerization inhibiting action is an oxygen-containing gas or a nitrogen oxide-containing gas.

3. A method according to claim 1 or 2, wherein said gas having a polymerization inhibiting action has a temperature which is higher by 0 to 30° C. than the temperature of the gas-phase portion.

4. A method according to claim 1, wherein said apparatus is an apparatus for handling (meth)acrylic esters.

5. A method according to claim 1, wherein said apparatus is distillation columns or decomposition reactors for (meth) acrylic esters.

* * * * *